United States Patent
Davies

(10) Patent No.: US 11,158,114 B2
(45) Date of Patent: Oct. 26, 2021

(54) MEDICAL IMAGING METHOD AND APPARATUS

(71) Applicant: Canon Medical Systems Corporation, Otawara (JP)

(72) Inventor: Ross Davies, Edinburgh (GB)

(73) Assignee: Canon Medical Systems Corporation, Otawara (JP)

(*) Notice: Subject to any disclaimer, the term of this patent is extended or adjusted under 35 U.S.C. 154(b) by 0 days.

(21) Appl. No.: 16/417,263

(22) Filed: May 20, 2019

(65) Prior Publication Data
US 2020/0372700 A1    Nov. 26, 2020

(51) Int. Cl.
| | | |
|---|---|---|
| G06T 3/40 | (2006.01) | |
| G06T 15/08 | (2011.01) | |
| G06T 15/06 | (2011.01) | |
| G06T 7/70 | (2017.01) | |
| G16H 30/40 | (2018.01) | |

(52) U.S. Cl.
CPC ............... *G06T 15/08* (2013.01); *G06T 7/70* (2017.01); *G06T 15/06* (2013.01); *G16H 30/40* (2018.01); G06T 2207/10081 (2013.01); G06T 2207/10088 (2013.01); G06T 2207/10116 (2013.01); G06T 2207/20081 (2013.01); G06T 2207/20084 (2013.01); G06T 2210/41 (2013.01)

(58) Field of Classification Search
CPC ....... G06T 3/40; G06T 3/4053; G06T 7/0012; G06T 7/10; G06T 7/12; G06T 7/13; G06T 7/70; G06T 15/06; G06T 15/08; G06T 2207/10081; G06T 2210/36; G06T 2210/41; G06T 2207/10088; G06T 2207/10116; G16H 30/40
See application file for complete search history.

(56) References Cited

U.S. PATENT DOCUMENTS 7,301,538 B2    11/2007  Buyanovskiy
7,843,452 B2    11/2010  Li
(Continued)

FOREIGN PATENT DOCUMENTS

| JP | 2006-55213 A | 3/2006 |
|---|---|---|
| JP | 2013-81716 A | 5/2013 |
| JP | 2017-503244 A | 1/2017 |

OTHER PUBLICATIONS

Cabello, Jorge, and Sibylle I. Ziegler. "Advances in PET/MR instrumentation and image reconstruction." The British journal of radiology 91.1081 (2018): 20160363 (Year: 2018).*

(Continued)

Primary Examiner — Diane M Wills
(74) Attorney, Agent, or Firm — Oblon, McClelland, Maier & Neustadt, L.L.P.

(57) ABSTRACT

An image processing apparatus for generating an image from volumetric data includes processing circuitry configured to: obtain a volumetric data set; obtain a heterogeneity map based on the volumetric data set; determine positions of a set of non-periodic sampling points using the heterogeneity map; generate from the volumetric data set a set of sampled data values based on the determined positions of the non-periodic sampling points; and generate an image data set by performing an aggregation process to generate a set of image data points from the set of sampled data values.

20 Claims, 6 Drawing Sheets

(56) References Cited

U.S. PATENT DOCUMENTS

| | | | | |
|---|---|---|---|---|
| 9,035,945 | B1* | 5/2015 | McKenzie | G06T 15/08 345/424 |
| 2006/0056726 | A1 | 3/2006 | Fujiwara et al. | |
| 2008/0246770 | A1* | 10/2008 | Kiefer | G06T 15/50 345/441 |
| 2013/0129037 | A1 | 5/2013 | Nakanishi | |
| 2015/0145864 | A1 | 5/2015 | Buyanovskiy | |
| 2016/0171338 | A1 | 6/2016 | Mine et al. | |
| 2016/0174902 | A1* | 6/2016 | Georgescu | G06T 7/0012 600/408 |
| 2017/0169602 | A1 | 6/2017 | Blackmon et al. | |
| 2017/0352181 | A1* | 12/2017 | Vetter | G06T 17/005 |

OTHER PUBLICATIONS

Chen etal, "Hardware-Accelerated Adaptive EWA Volume Splatting", IEEE Visualization, Oct. 10-15, 2004 (Year: 2004).*

Madankan, Reza, et al. "Accelerated magnetic resonance thermometry in the presence of uncertainties" Physics in Medicine & Biology 62.1 (2016). (Year: 2016).*

Mitchell S A, Rand A, Ebeida M S and Bajaj C 2012 Variable radii poisson-disk sampling, Proc, of the 24th Canadian Conf, on Computational Geometry vol. 5 (Year: 2012).*

Ostromoukhov, Victor, Charles Donohue, and Pierre-Marc Jodoin. "Fast hierarchical importance sampling with blue noise properties " ACM Transactions on Graphics (TOG) 23.3 (2004): 488-495 (Year: 2004).*

"REYES Attributes", Renderrnan, 2019, https://renderman.pixar.com/resources/RenderMan_20/attributes.html, 28 pages.

'Colors of Noise', Retrieved from Wikipedia: https://en.wikipedia.org/wiki/Colors_of_noise, May 31, 2019, 6 pages.

'Aliasing', Retrieved from Wkipedia: https://en.wikipedia.org/wiki/Aliasing, May 31, 2019, 3 pages.

'Wang tile', Retrieved from Wikipedia: https://en.wikipedia.org/wiki/Wang_tile, May 31, 2019, 4 pages.

Kopf, J. et al., "Recursive Wang Tiles for Real-Time Blue Noise", ACM Transactions on Graphics (Proceedings of SIGGRAPH 2006), vol. 25, No. 3, 2006, 10 pages.

* cited by examiner

MEDICAL IMAGING METHOD AND APPARATUS

FIELD

Embodiments described herein relate generally to an apparatus and method for producing images for display or analysis, in particular medical images.

BACKGROUND

Techniques for producing images for display from imaging data sets are well known. For example in the context of medical imaging, there are a wide range of rendering or sampling techniques for producing from volumetric imaging data sets images that can be displayed on display screens.

In the context of medical imaging, volumetric imaging data sets can be produced using a wide range of imaging modalities for example, but not limited to using computerized tomography (CT) scanners, X-ray modalities, ultrasound scanners, or positron emission tomography (PET) scanners.

The images that can be produced can take a variety of forms, and can include two-dimensional or three-dimensional representations for display on two-dimensional display screens. In the context of medical imaging, the images can be produced for a variety of purposes but are often used by medical practitioners for diagnostic or monitoring purposes and/or to assess particular medical conditions that may or may not be present. As well as being computationally intensive, sampling or rendering techniques used in medical imaging need to produce images that are convincing or acceptable to the medical practitioner whilst also accurately representing anatomical or other features of the subject of the image. Such images may need to represent time-dependent processes such as blood flow, heart beat or other processes accurately and may also be subject to registration or other processes.

Processes for generating images from data, for example volumetric medical imaging data, also need at some stage in the process to take into account the hardware on which the image is to be displayed, for example the resolution of the display on which the image is to be displayed.

It is known to produce medical image data sets with a desired resolution, for example a desired number or spacing of pixel data points, suitable for display on a device with a particular resolution. Medical imaging data sets with a desired resolution can be produced, for example, by selecting a suitable sampling of the original data and/or by producing a data set of a different resolution and applying suitable upscaling or downscaling processes to that data set, for instance suitable interpolation, extrapolation or sampling processes.

Known techniques for producing image data sets with a desired resolution may produce significant artifacts and/or may be computationally intensive.

Volume rendering is usually done using a regular grid sampling. An advantage of such regular grid sampling may be that mapping to screen pixels is straightforward. A disadvantage of regular grid sampling may be that aliasing may be introduced.

Aliasing is an effect which may cause significant artifacts due for example to resonant under-sampling.

FIG. 1 is a plot that illustrates schematically an example of aliasing. Signal amplitude is plotted against time. A dotted line 10 shows a sine curve which is representative of a signal to be sampled. The sine curve is sampled at a set of sample points 12a to 12n, which are joined by solid line 14. The sampling of the sine curve may be considered to be an under-sampling. It can be seen in FIG. 1 that the sampled points 12a to 12n have an envelope that has a lower frequency than the frequency of the sine curve. An additional, unwanted frequency may therefore be introduced by the under-sampling.

Downsizing may worsen aliasing effects. Downsizing may comprise a process of reducing a higher-resolution set of sampled points to a lower-resolution set of sampled points. Downsizing is usually performed using power-of-two factors in order to reduce both complexity and potential visual artefacts. However, downsizing usually still causes some artefacts, particularly around edges or other features that include high frequency features or non-continuous changes or textures. Power-of-two downsizing may be considered to be non-granular because the dimensions of the entire image are reduced by a factor of two (for example, a 512×512 image becomes a 256×256 image). This means that the least impactful level of downsampling that can be achieved through power-of-two downsampling reduces the number of pixels in the image to one quarter of the original number of pixels.

Rendering performed by regular grid sampling (for example, using downsizing) may be non-progressive. There may be no information re-use when rendering a higher resolution after completing a lower resolution render, which can be wasteful of processing resources.

An alternative to using regular grid sampling may be to use a non grid-based sampling pattern. However, it may be difficult to reconstruct non grid-based sampling patterns into a uniform grid. Reconstruction of a non grid-based sampling pattern using Delauney triangulation and interpolation may be slow.

There is an increasing need to accommodate high-definition monitors without losing performance or image quality. From a user perspective it may be desirable for an image to be consistent regardless of the resolution of the screen on which it is displayed. Users may expect to be able to view images on screens of a range of different types at different times, for example 4K displays, retina displays, high definition displays, mobile device screens and desktop monitors. The computational burden of producing images for some higher definition screens is already considerable, and may be increased by the desire to be able to view the same image data in consistent fashion on screens of different resolutions.

BRIEF DESCRIPTION OF THE DRAWINGS

Embodiments are now described, by way of non-limiting example, and are illustrated in the following figures, in which.

DETAILED DESCRIPTION OF THE DRAWINGS

Certain embodiments provide an image processing apparatus for generating an image from volumetric data comprising processing circuitry configured to: obtain a volumetric data set; obtain a heterogeneity map based on the volumetric data set; determine positions of a set of non-periodic sampling points using the heterogeneity map; generate from the volumetric data set a set of sampled data values based on the determined positions of the non-periodic sampling points; and generate an image data set by performing an aggregation process to generate a set of image data points from the set of sampled data values.

Certain embodiments provide a method of generating an image from volumetric data comprising: obtaining a volumetric data set; obtaining a heterogeneity map based on the volume data; determining positions of a set of non-periodic sampling points using the heterogeneity map; generating from the volumetric data set a set of sampled data values based on the determined positions of the non-periodic sampling points; and generating an image data set by performing an aggregation process to generate a set of image data points from the set of sampled data values.

Figure 1:
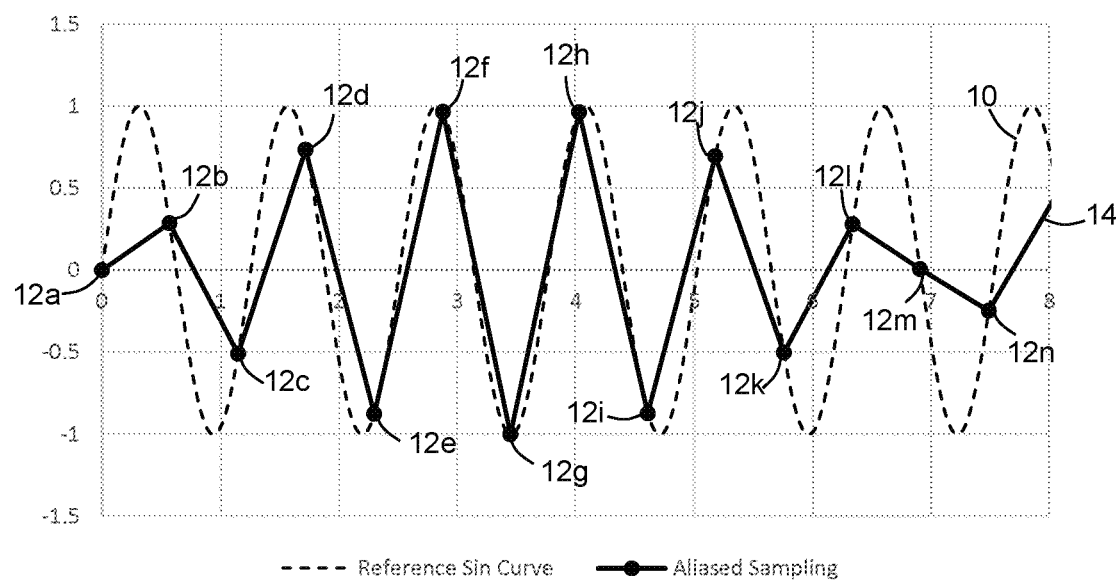
FIG. 1 is a plot schematically illustrating an example of aliasing.
Figure 2:
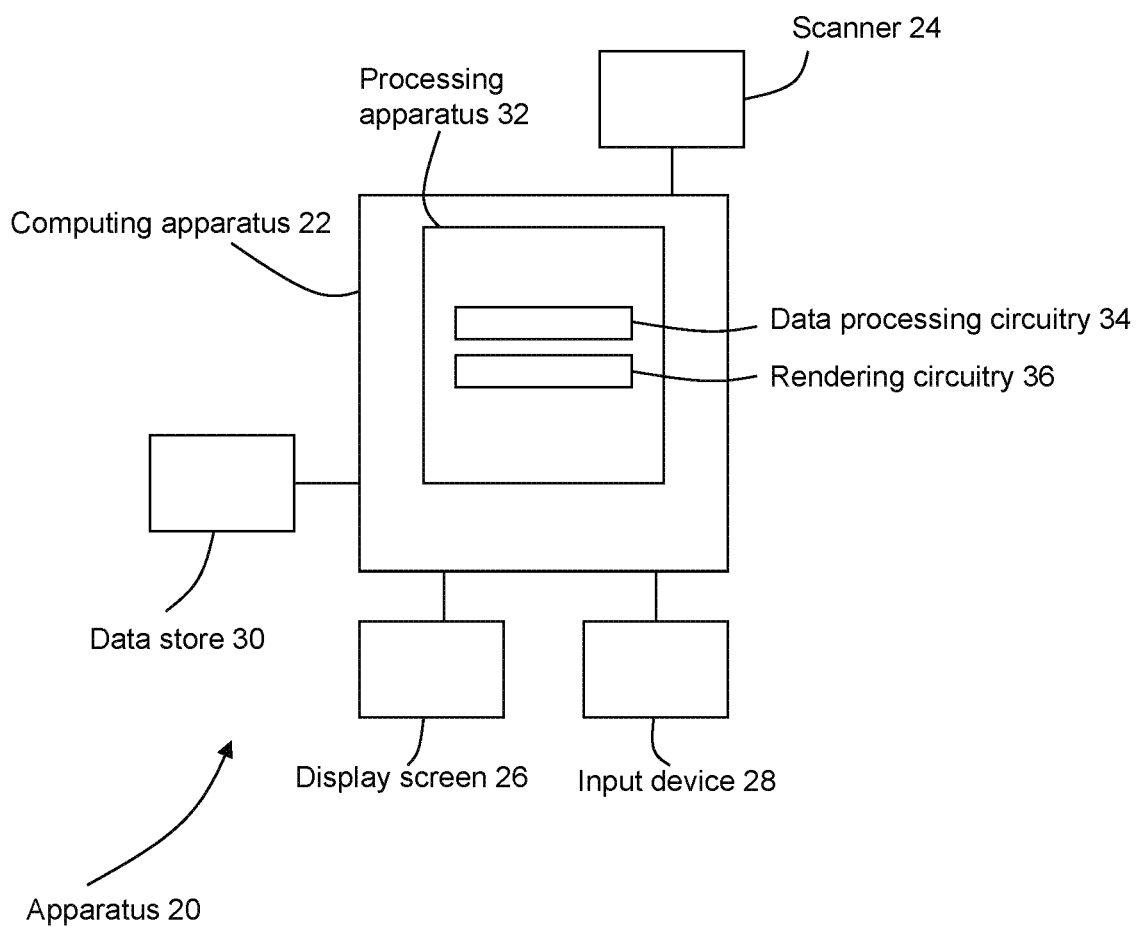
FIG. 2 is a schematic diagram of an apparatus according to an embodiment.

An image processing apparatus 20 according to an embodiment is illustrated schematically in FIG. 2.

The image processing apparatus 20 comprises a computing apparatus 22, in this case a personal computer (PC) or workstation, which is connected to a scanner 24, one or more display screens 26 and an input device or devices 28, such as a computer keyboard, mouse or trackball.

The scanner 24 may be any scanner that is configured to perform medical imaging. The scanner 24 is configured to generate image data that is representative of at least one anatomical region of a patient or other subject. The scanner may be configured to obtain two-dimensional or three-dimensional image data in any imaging modality. For example, the scanner 24 may comprise a magnetic resonance (MR) scanner, CT (computed tomography) scanner, cone-beam CT scanner, X-ray scanner, ultrasound scanner, PET (positron emission tomography) scanner or SPECT (single photon emission computed tomography) scanner. In further embodiments, the scanner may generate any type of image data, which may not be medical image data.

In the present embodiment, image data sets obtained by the scanner 24 are stored in data store 30 and subsequently provided to computing apparatus 22. In an alternative embodiment, image data sets are supplied from a remote data store (not shown) which may form part of a Picture Archiving and Communication System (PACS). The data store 30 or remote data store may comprise any suitable form of memory storage.

Computing apparatus 22 comprises a processing apparatus 32 for processing of data, including image data. The processing apparatus comprises a central processing unit (CPU) and Graphical Processing Unit (GPU).

The processing apparatus 32 provides a processing resource for automatically or semi-automatically processing image data sets.

The processing apparatus 32 includes data processing circuitry 34 configured to process volumetric imaging data, and rendering circuitry 36 configured to render an image from the volumetric imaging data.

In the present embodiment, the circuitries 34, 36 are each implemented in the CPU and/or GPU by means of a computer program having computer-readable instructions that are executable to perform the method of the embodiment. In other embodiments, the various circuitries may be implemented as one or more ASICs (application specific integrated circuits) or FPGAs (field programmable gate arrays).

The computing apparatus 22 also includes a hard drive and other components of a PC including RAM, ROM, a data bus, an operating system including various device drivers, and hardware devices including a graphics card. Such components are not shown in FIG. 2 for clarity.

Figure 3:
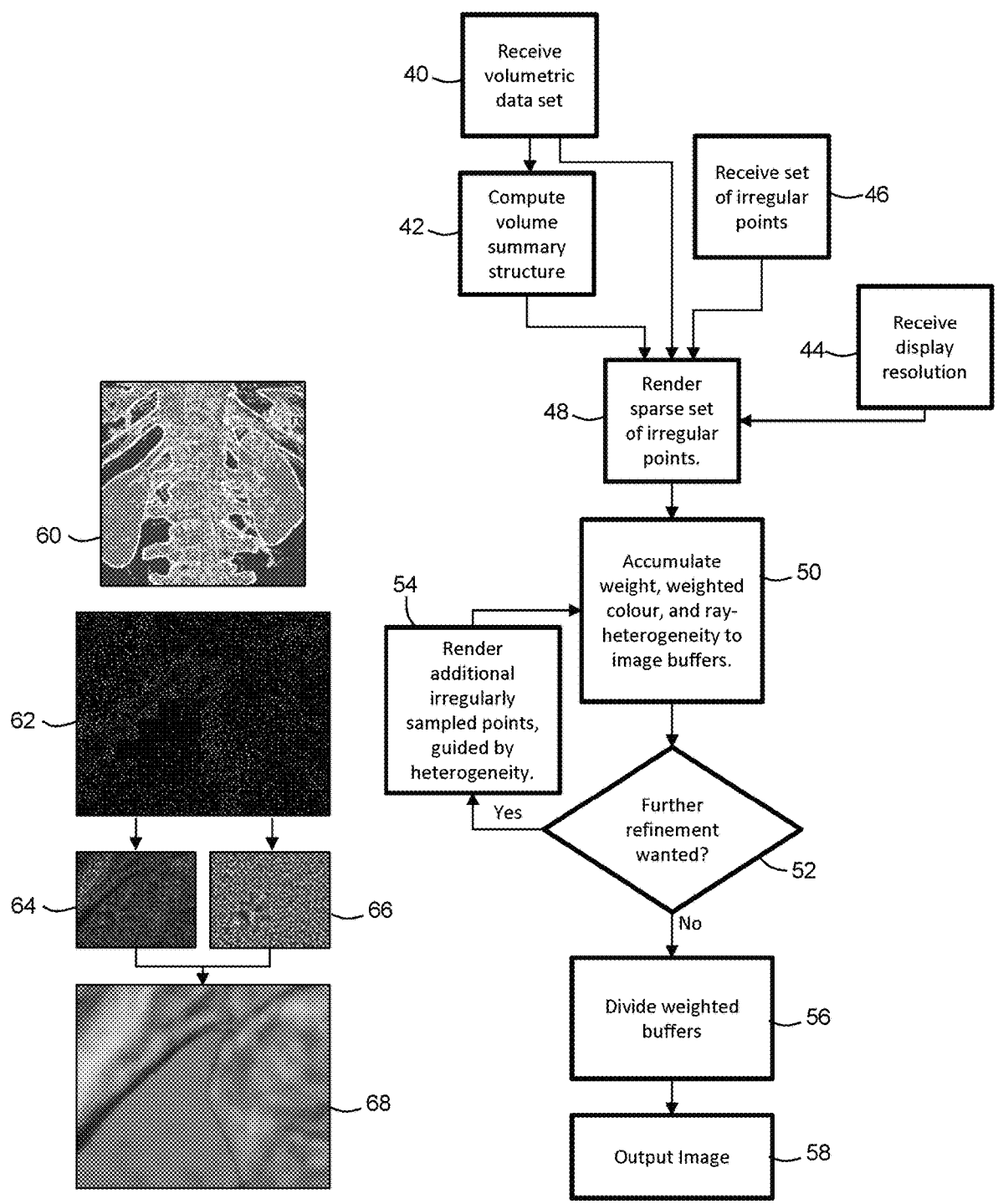
FIG. 3 is a flow chart illustrating in overview a method of an embodiment.

FIG. 3 is a flow chart illustrating in overview an image rendering method of an embodiment. The image processing apparatus of FIG. 2 is configured to perform an image rendering method as illustrated in FIG. 3.

At stage 40 of FIG. 3, the data processing circuitry 34 receives a set of volumetric imaging data, which may be referred to as a volumetric data set. In the present embodiment, the volumetric data set comprises a set of volumetric medical imaging data that has been obtained using scanner 24 and stored in data store 30. In further embodiments, the volumetric data set may comprise any volumetric medical imaging data of an suitable modality, and may be received from any suitable data store. In other embodiments, the volumetric data set may comprise any form of imaging data, which may not be medical.

At stage 42, the data processing circuitry 34 computes a volume summary structure from the volumetric data set. The volume summary structure is a data set providing summary information about the volumetric data set. The volume summary structure is volumetric. The volume summary structure comprises data at a lower resolution than the volumetric data set itself.

The volume summary structure is a low resolution blocked structure storing coarse information. In some embodiments, the volume summary structure is multi-layer. Each block may be representative of a sub-region of the volume represented in the volumetric data set, for example a cuboidal sub-region. For each block, the volume summary structure may store one or more values for one or more parameters that provide a characterization of an amount of information in that block, for example an amount of detail in that block and/or information about whether one or more transitions between objects are present in that block.

The data processing circuitry 34 computes the volume summary structure by processing the volumetric imaging data to obtain information relevant to one or more types of heterogeneity in the volumetric imaging data and/or in the anatomical region that was scanned to obtain the volumetric imaging data. For example, the anatomical region may obtain two or more different tissue types, and the volumetric imaging data may be heterogeneous in that it includes regions that are representative of each of the tissue types, and have different image properties in dependence on the tissue type represented.

In the present embodiment, the computing of the volume summary structure comprises a segmentation of one or more tissue types in the volumetric data set. The computing of the volume summary structure comprises classifying by tissue type each of a plurality of points within the volumetric data set. Any suitable segmentation and/or classification method may be used to obtain the volume summary structure. The values stored for each block may indicate whether transitions between objects are present in the block. By considering segmentation in the volume summary structure, it may be the case that transitions between objects (even objects of similar colors) remain sharp in the resulting rendered image.

In other embodiments, the computing of the volume summary structure comprises processing the volumetric data set to obtain any suitable image parameter for different parts of the volumetric data set, for example by obtaining values for dynamic range, transfer functions, or wavelet indices at each of a plurality of points within the volumetric data set. As an example, maximum color gradient within a block may be used as a measure of internal discontinuities, and how hard those internal discontinuities may be. Wavelet indices may give an idea of the amount of detail present in the block.

In the present embodiment, the volume summary structure is relatively low-resolution. To obtain the volume summary structure, image properties of the volumetric data set are computed at a resolution that is lower than that of the volumetric data set itself. In other embodiments, the volume summary structure may be computed at the same resolution as the volumetric data set, or at a further resolution.

In the present embodiment, the volume summary structure is generated by the data processing circuitry 34 as part of the rendering process of FIG. 3. In other embodiments, the volume summary structure may be pre-computed (for example, by a different computing apparatus) and is provided to the data processing circuitry 34 along with the volumetric data set.

At stage 44, the rendering circuitry 36 receives a selection of an image resolution, for example a number of pixels to be included in a target image. The selected image resolution may comprise, for example, 1920×1080 pixels (High Definition), 3840×2160 pixels (4K Ultra High Definition), 2732×2048 (iPad Pro Retina), or any suitable image resolution. The selected image resolution may be an image resolution that is appropriate for a display screen to be used, for example display screen 26 or any suitable display screen. For example, the image resolution may be selected for use with a desktop, laptop or tablet computer. The image resolution may be selected for use with a mobile device. The image resolution may be selected for use in a virtual reality application, for example for use in a virtual reality headset.

In some embodiments, the data processing circuitry 34 already knows the resolution to be used, and stage 44 is omitted from the process of FIG. 3. In some embodiments, the selected resolution may be stored in the data processing circuitry 34 or elsewhere in the computing apparatus 22. In other embodiments, the resolution is selected by a user. The user inputs the resolution to the computing apparatus 22, for example by using input device 28.

The rendering circuitry 36 may also receive one or more image rendering parameters, for example a camera position from which the target image is to be rendered, and/or colors or textures to be used in rendering. The rendering circuitry 36 may receive one or more transfer functions or rendering pre-sets.

At stage 46, the rendering circuitry 36 receives or generates a set of points on a two-dimensional plane, which may be referred to as initial sampling points. The two-dimensional plane is representative of a plane on which the target image is to be rendered. The two-dimensional plane may be referred to as an image plane.

The initial sampling points are distributed on the image plane in a non-periodic fashion. The distribution of the initial sampling points may be said to be irregular. The set of initial sampling points may be said to be sparse. The initial sampling points may be referred to as irregular points or non-periodic points. The initial sampling points are not distributed in accordance with a regular pattern such as a regular grid. The initial sampling points are not positioned at regular, equidistant intervals. Instead, the spacings between the sampling points differ from each other.

The rendering circuitry 36 stores a position for each initial sampling point in the set of initial sampling points.

The set of initial sampling points that is received or generated at stage 46 may be considered to be a small set of irregular sampling points. The set of initial sampling points may comprise a number of sampling points that is considerably less than a number of pixels to be included in the target image.

In the present embodiment, the initial sampling points are distributed on the image plane in accordance with a Blue Noise distribution. In computer graphics, Blue Noise may be taken to mean a random sampling having minimal low-frequency components, and no concentrated spikes of energy. It is known that low-frequency components may lead to aliasing artifacts. Energy spikes mean that the sampling density is non-uniform.

Figures 4A, 4B:
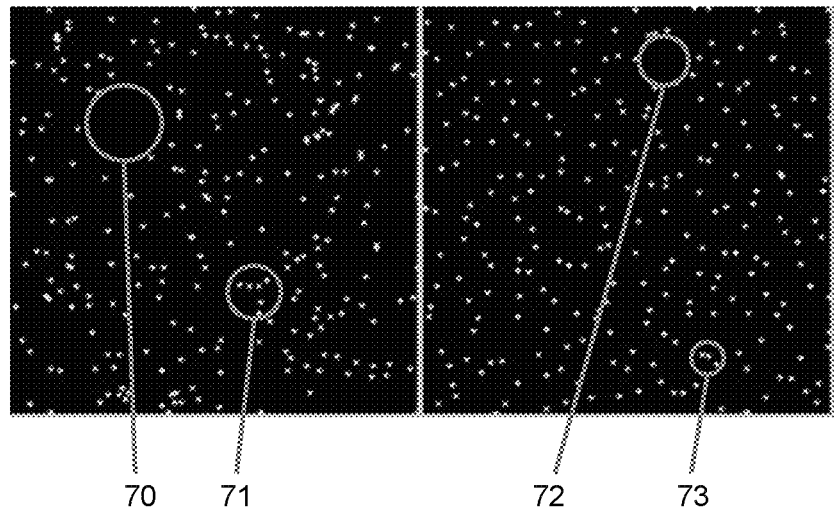
FIG. 4a is an illustration of random points.
FIG. 4b is an illustration of a jittered grid of points.

FIGS. 4a to 4d are illustrative examples of different distributions of points on a two-dimensional plane. FIG. 4a shows a random point distribution. In a random distribution such as that shown in FIG. 4a, it is expected that energy spikes may create areas of under-sampling and over-sampling. Energy spikes may comprise regions having a higher sampling density than surrounding regions. In FIG. 4a, a first circle 70 is used to indicate an area of under-sampling. A second circle 71 is used to indicate an area of over-sampling.

FIG. 4b shows a jittered grid. A jittered grid may comprise a set of points that are offset from regular grid positions by different amounts, for example by applying a respective random offset quantity and offset direction to each point in a regular grid. In the jittered grid of FIG. 4b, energy spikes are smaller than those in the random distribution of points in FIG. 4a. However, some energy spikes are still present. A first circle 72 in FIG. 4b is used to indicate an area of under-sampling. A second circle 73 in FIG. 4b is used to indicate an area of over-sampling.

Figures 4C, 4D:
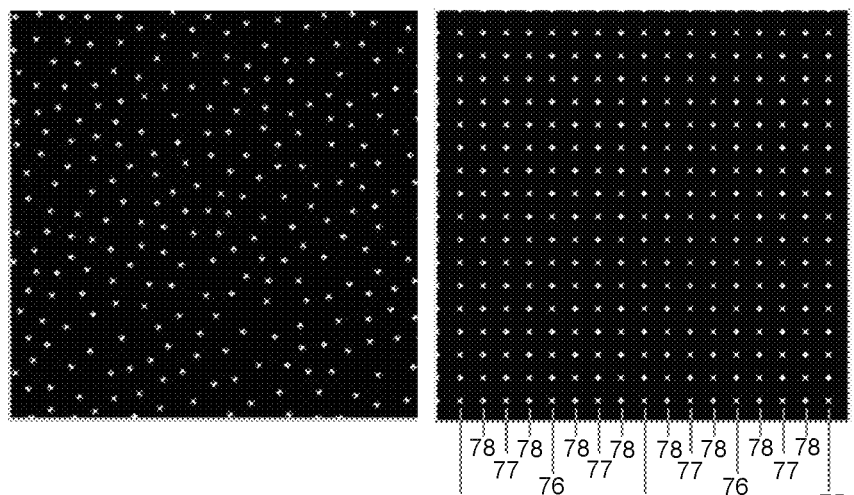
FIG. 4c is an illustration of blue noise.
FIG. 4d is an illustration of a regular grid of points.

FIG. 4c shows a distribution of points that is generated using Blue Noise sampling. The use of Blue Noise produces an aperiodic, irregular spacing with substantially no energy spikes. Blue Noise sampling patterns may be very good at mitigating aliasing due to resonant under-sampling.

FIG. 4d shows a regular grid of points. The regular spacing of the points of FIG. 4d means that there are multiple resonant frequencies of the grid, any of which may alias. A set of lines 75, 76, 77, 78 are shown on FIG. 4d. Different lengths of line are used to illustrate different resonant frequencies of the regular grid. A first resonant frequency may be obtained by taking every eighth line of points (lines 75). A second resonant frequency may be obtained by taking every fourth line (lines 75 and 76). A third resonant frequency may be obtained by taking every second line (lines 75, 76, 77). A fourth frequency may be obtained by taking every line (lines 75, 76, 77, 78).

The set of initial sampling points of stage 46 of FIG. 3 are distributed in a pattern that is consistent with Blue Noise. The initial sampling points are obtained or generated using a Blue Noise sampling process. In the present embodiment, the initial sampling points are obtained using a pre-computed set of progressive Blue Noise tiles, which in the present embodiment are recursive Wang tiles.

Wang tiles provide a mechanism for producing an aperiodic tiling of a surface, Recursive Wang tiles have been presented as a method for producing real-time Blue Noise. Recursive Wang tiles allow for filling an infinite plane with a Blue Noise approximate of any point density.

The recursive Wang tiles may be used to obtain a Blue Noise sampling pattern in any suitable manner, for example by using a method as described in Kopf et al, Recursive Wang tiles for real-time blue noise, Proceeding SIGGRAPH '06, ACM Transactions on Graphics, Volume 25 Issue 3, July 2006 Pages 509-518.

In the present embodiment, positions of the initial non-periodic sampling points are in accordance with a Blue Noise distribution. In other embodiments, any suitable non-periodic distribution may be used, for example any suitable random or pseudorandom distribution. In some embodiments, the positions of the initial sampling points may be determined by a jittered grid process. In other embodiments, any suitable method may be used to obtain the positions of the set of initial sampling points, for example any suitable aperiodic tiling.

At stage 48, the rendering circuitry 36 performs a rendering process for each of the set of initial sampling points. In the present embodiment, the rendering process for each initial sampling point comprises performing a ray-casting process for that initial sampling point.

The rendering circuitry 36 casts rays into the volume represented by the volumetric data set from a camera position. Each ray corresponds to a respective one of the initial sampling points. The path of each ray intersects a respective one of the initial sampling points on the image plane.

Each ray steps through the volume represented by the volumetric data set in incremental steps. For example, a step size along the ray may be the same as the voxel spacing in the volumetric data set. Each incremental point along the ray may be referred to as a ray sampling point.

At each ray sampling point, the ray samples the volumetric data set. In the present embodiment, the ray samples a respective color value at each sampling point. The color value may be obtained by using a transfer function to relate color value to intensity. The color value at the sampling point may be interpolated from voxels in the neighborhood of the sampling point. An opacity value may also be sampled at each sampling point. In other embodiments, any suitable parameter may be sampled at the ray sampling points. For example, a grayscale intensity may be sampled at the ray sampling points.

For each ray, color is accumulated along the ray by combining the color values at the ray sampling points along the ray. A color value for each of the initial sampling points is obtained by accumulating color values along the ray associated with that initial sampling point. Image 62 of FIG. 3 represents color values for a set of initial sampling points (shown in FIG. 3 as greyscale) in a region of an image plane. The color values may also be referred to as sampled data values.

The rendering circuitry 36 splats the color values for the initial sampling points into an accumulation buffer with a weighted fall-off. The accumulation buffer may be referred to as a weighted color accumulation buffer. The weighted color accumulation buffer is a two-dimensional buffer comprising a plurality of image data points. The image data points may be considered to correspond to pixels of the target image, or to pixels of a higher-resolution image. The image data points may therefore also be referred to as pixels. The number of image data points in the weighted color accumulation buffer is greater than the number of initial sampling points.

In the splatting process, color from each initial sampling point is spread over nearby image data points (or pixels) of the weighted color accumulation buffer. The color at each sampling point may be considered to form a two-dimensional disk in the image plane which spreads across multiple image data points of the weighted color accumulation buffer (and therefore spreads across multiple pixels of the image to be rendered).

A weighting function is applied to each of the initial sampling points. The weighting function may be considered to define the extent and profile of the disk of color that is associated with each of the initial sampling point. The weighting function falls off with distance from the initial sampling point (as measured in the image plane).

Figure 5:
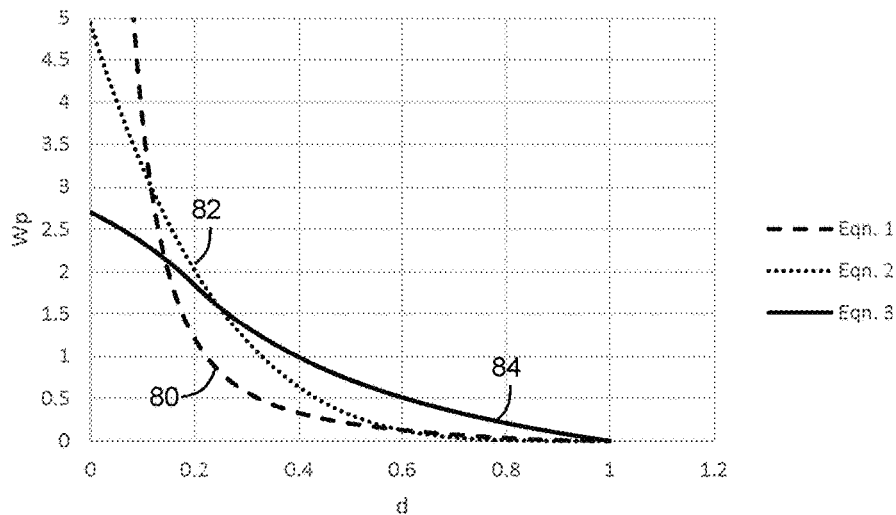
FIG. 5 is a plot showing examples of weighting functions.

FIG. 5 plots some examples 80, 82, 84 of weighting functions having different fall-offs. Pixel weight $W_p$ is plotted against distance d from the initial sampling point.

A first line 80 plots a first weighting function which is defined by Equation 1 below:

$$W_p = (-\ln d)^2 \left(1.0016 d^2 - 0.221345 d + \frac{2.88461}{40*d+1} + 0.151608\right) \quad \text{(Equation 1)}$$

Equation 1 is an example of a weighting function having a relatively steep fall-off. If a weighting function with a steep fall-off is used, color from each initial sampling point will be splatted only onto pixels that are very close to the initial sampling point.

A second line 82 plots a second weighting function which is defined by Equation 2 below:

$$W_p = \frac{\pi^2 (1-d)^4}{2} \quad \text{(Equation 2)}$$

A third line 84 plots a third weighting function which is defined by Equation 3 below:

$$W_p = 3 \frac{2(1-d) - 1.6}{1 + |2(1-d) - 1.6|} + 1.846 \quad \text{(Equation 3)}$$

Equation 3 is an example of a weighting function having a less steep fall-off, which may be referred to as a shallower weighting function. If a shallower weighting function is used, color from each initial sampling point may be spread across a higher number of pixels than if a steeper weighting function were used. The shallower weighting function may yield more blur in a resulting image than a steeper weighting function. The shallower weighting function may result in less noise than a steeper weighting function.

In other embodiments, any suitable weighting function or combination of weighting functions may be used.

When splatting the color of an initial sampling point into pixels of the weighted color accumulation buffer, the weighting function is used to obtain a pixel weight $W_p$ for each pixel of the weighted color accumulation buffer. The pixel weight $W_p$ is dependent on the distance d from the image pixel to the true initial sampling point. The color value for the initial sampling point is combined with the pixel weight $W_p$, for example by multiplying the color value by the pixel weight $W_p$. A larger pixel weight is representative of a stronger color.

In addition to accumulating colors in the weighted color accumulation buffer, the rendering circuitry 36 accumulates the pixel weights $W_p$ in a further accumulation buffer, which may be referred to as a weights accumulation buffer or accumulated weights buffer. The weights accumulation buffer has the same number of pixels as the weighted color accumulation buffer.

A pixel of the weighted color accumulation buffer may receive color contributions from more than one of the initial sampling points. A pixel of the weights accumulation buffer may receive corresponding weights from the same more than one of the initial sampling points.

In the present embodiment, a color value for each ray is obtained and the color value for the ray is splatted onto the weighted color accumulation buffer. In other embodiments, color values for each individual ray sampling point on the ray may be splatted onto the weighted color accumulation buffer. A weighting function may be applied to each of the individual ray sampling points.

In other embodiments, any suitable buffer or buffers may be used. Values of intensity, color, weight or any other suitable parameter may be stored in a buffer or buffers.

In further embodiments, any suitable aggregation process may be performed to obtain pixel color values using color values for the ray sampling points. The aggregation process may be weighted in any suitable manner. Any suitable fill process may be used instead of splatting. Although ray casting is described above, in other embodiments any suitable image rendering process may be used in which an image is rendered using non-periodic sampling points.

At stage 50, while rendering, the rendering circuitry 36 also samples from the volume summary structure to form a ray-region heterogeneity metric.

Figure 6:
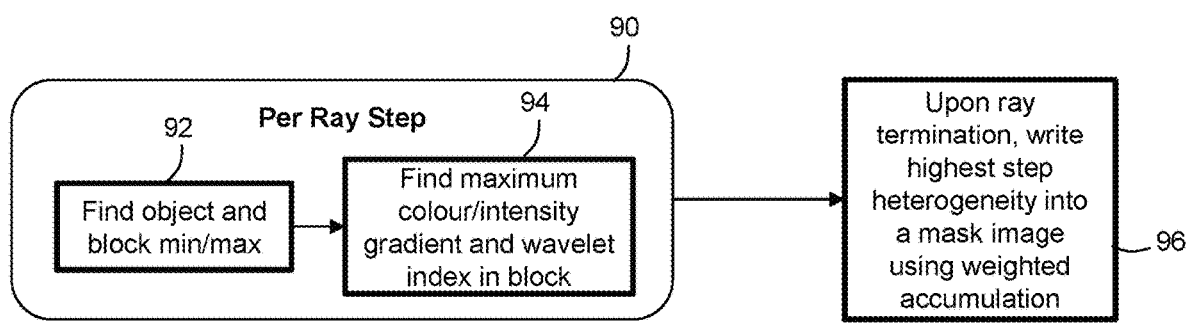
FIG. 6 is a flow chart illustrating in overview a method of computing a ray-region heterogeneity metric in accordance with an embodiment.

FIG. 6 is a flow chart illustrating in overview a method of computing values for a ray-region heterogeneity metric in accordance with an embodiment. The method of FIG. 6 is repeated for each of the initial sampling points.

The method of FIG. 6 comprises a processing stage 90 which is repeated for each step of the ray, and an accumulation stage 96 which accumulates values for the whole ray. The processing stage 90 comprises two sub-stages 92 and 94.

The rendering circuitry 36 performs stage 90 for each ray sampling point. At sub-stage 92, the rendering circuitry 36 finds an object and block minimum or maximum. The rendering circuitry 36 identifies a block (a sub-region of the volume) in which the ray sampling point is located. The rendering circuitry 36 finds a maximum intensity value and minimum intensity value for the block. The rendering circuitry 36 uses the maximum intensity value and minimum intensity value to determine a range of intensity values that are present in the block. If the range of intensity values is known, then a possible range of colors that may be accumulated by ray sampling points within that block may be known, which may allow the rendering circuitry 36 to approximate an amount of detail that may be present within the block.

For example, a segmentation may have been performed on the volume, the segmentation identifying a number of different labels which may be applied to individual voxels. A group of voxels having the same label may be referred to as an object or as a segmentation object. A set of material properties is applied to voxels within each object.

A given block may comprise voxels from one or more segmentation objects. The rendering circuitry 32 may find minimum and maximum intensity values (for example, minimum and maximum greyscale values) in a given block and map the intensity values to a respective set of color ranges for each object. The resulting color ranges may be used to approximate an amount of detail in the block.

In one example, a block has a minimum intensity value of 0, and a maximum intensity value of 1000, with two objects present. One of those objects is uniformly transparent throughout the 0 to 1000 range. The other object has only small variations in color through the 0 to 1000 range. In this example, the block may be treated as homogeneous due to the small amount of color variation, even though the data range of 0 to 1000 may be considered to be a large range of intensity values.

An output of stage 92 is an identification of a block on which sub-stage 94 is to be performed and the range of intensity values and/or color values for that block.

At sub-stage 94, the rendering circuitry 36 determines a value for a heterogeneity metric in the block identified in sub-stage 92. In the present embodiment, the heterogeneity metric is a function of color gradient, intensity gradient and wavelet index within the block. The heterogeneity metric may be referred to as a ray-region heterogeneity metric, since it relates to heterogeneity in a region surrounding a ray sampling point.

The rendering circuitry 36 finds in the block identified at sub-stage 92 a maximum color gradient, a maximum intensity gradient, and a maximum wavelet index. The rendering circuitry 36 calculates a value for the heterogeneity metric based on the values for maximum color gradient, maximum intensity gradient and maximum wavelet index for the identified block.

In other embodiments, any suitable heterogeneity metric may be used. The heterogeneity metric may be any function which represents a heterogeneity within the block, for example a difference in color, a difference in intensity, a difference in texture. The heterogeneity metric may be any function which represents a heterogeneity in the anatomical region represented by the block, for example a difference in tissue type.

In some embodiments, values in the volume summary structure (for example, values for maximum color gradient, maximum intensity gradient and maximum wavelet index) are summarized into values for one or more dimensionless parameters, which may be considered to describe local heterogeneity.

Stage 90 is repeated for each step of the ray. Each instance of stage 90 outputs a respective value for the heterogeneity metric for a respective ray sampling point. The value for the heterogeneity metric may be referred to as a step heterogeneity.

At stage 96, once the ray has terminated, the rendering circuitry 36 determines the highest value for the heterogeneity metric that has been obtained for any ray sampling point in the ray. The highest value for the heterogeneity metric may be referred to as the highest step heterogeneity.

The rendering circuitry 36 writes the highest step heterogeneity for the ray into a mask image using weighted accumulation. While accumulating color along the ray, the heterogeneity is also accumulated as an independent value. The ray heterogeneity is then splatted in the same way as the color splatting described above.

The mask image may also be referred to as a heterogeneity map. In the present embodiment, the heterogeneity map comprises a smaller buffer than the full-size image buffers used for the weighted colors and weights.

Image 60 in FIG. 3 represents the heterogeneity map. The heterogeneity map may be considered to be a two-dimensional projection of the volume summary structure. The heterogeneity map is a two dimensional map comprising a representation of value of the heterogeneity metric as a function of position. Values for accumulated heterogeneity have been calculated for each of the set of initial sampling points. The heterogeneity map provides a relatively low-resolution indication of which parts of the volumetric data set have high heterogeneity and which parts have low heterogeneity.

In the present embodiment, the values of the heterogeneity metric are determined using a ray-casting process as described above. A value for the heterogeneity metric at an initial sampling point is determined from the value or values for one or more parameters that are determined for points along a ray corresponding to that initial sampling point. In other embodiments, any suitable image rendering process may be used to obtain values of the heterogeneity metric from the volumetric data set.

We return to the flow chart of FIG. 3. The outputs of stage 50 of FIG. 3 are the weighted color accumulation buffer in which weighted color is accumulated; the weights accumulation buffer in which weight are accumulated; and the heterogeneity map.

Stage 52 is a decision stage. At stage 52, the rendering circuitry 36 determines whether further refinement is wanted. The heterogeneity map is used to guide refinement to areas of high heterogeneity.

It may be desirable to perform higher-resolution sampling in areas that are more heterogeneous. For example, if an initial low-resolution sampling has indicated that a large region of the volumetric data set is representative of a single material (for example, bone), it may not be considered necessary to perform more detailed sampling of that region. On the other hand, if initial sampling indicates that a region is highly heterogeneous, a higher-resolution sampling may be used to obtain more information about that region. For example, if a region is found to be a mix of tissue types, further sampling may be used to determine accurate boundaries between those tissue types.

In the present embodiment, at a first instance of stage 52, it is determined that further refinement is wanted. The set of initial sampling points used at stage 48 was small compared to the intended resolution of the final image. The rendering circuitry 36 determines that further sampling points should be used in the rendering.

The method of FIG. 3 proceeds to stage 54. At stage 54, the sampling circuitry 36 receives or generates further sampling points on the image plane. A distribution of the further sampling points is dependent on the heterogeneity map such that an average concentration of further sampled points varies with position in dependence on the value of the heterogeneity metric in the heterogeneity map.

The image plane is divided into a plurality of image regions. The heterogeneity map is used to determine whether each of the image regions is low-heterogeneity or high-heterogeneity. A sampling density for each image region is decided based on the heterogeneity map. A lower sampling density is applied to the low-heterogeneity regions than to the high-heterogeneity regions. Areas of high heterogeneity are sampled at higher density than areas of lower heterogeneity. In other embodiments, any suitable method of determining sampling density based on the heterogeneity map may be used.

In the present embodiment, the positions of the further sampling points are obtained using recursive Wang tiles as described above. A pattern of the further sampling points is consistent with Blue Noise. The further sampling points are generated using the sampling densities that have been determined using the heterogeneity map. Therefore, the density of the further sampling points varies with position in the image plane. The generating of the further sampling points takes into account the position of the initial sampling points, such that the Blue Noise distribution applies to the combination of the initial sampling points and the further sampling points. The use of a Blue Noise distribution of further sampling points may result in a distribution of sampling points (both initial sampling points and further sampling point) which is irregular and aperiodic.

In the present embodiment, the density of sampling points (and therefore the density of rays) is dependent on heterogeneity, but a step size used between ray sampling points in each ray is constant. In other embodiments, a step size between ray sampling points on a ray may also be dependent on heterogeneity.

The method of FIG. 3 returns to stage 50 once the further sampling points have been determined.

The rendering circuitry 36 casts a respective ray for each of the further sampling points. The rendering circuitry 36 determines a color for each ray using the same method as described above. The rendering circuitry 36 splats the colors for each further sampling point into the weighted color accumulation buffer using the weighting function as described above. The rendering circuitry 36 also stores the weights used for the color splatting in the weights accumulation buffer.

In the weighted color accumulation buffer and weights accumulation buffer, the weighted colors and weights for the further sampling points are added to the weighted colors and weights for the initial sampling points, thereby refining the initial rendering that was performed at the first instance of stage 50.

In the present embodiment, the rendering circuitry 36 calculates a value for the heterogeneity metric at each further sampling point using the method described above with reference to FIG. 6. The values for the heterogeneity metric are used to refine the heterogeneity map. In other embodiments, values for the heterogeneity metric are only calculated in the first instance of stage 50, and are not refined using the further sampling points. In further embodiments, any suitable method for determining the heterogeneity map may be used. The heterogeneity map may be calculated or re-calculated at any suitable stage of the rendering process.

After the second instance of stage 50, the method of FIG. 3 returns to stage 52, at which it is determined whether further refinement is wanted. For example, the decision of whether further refinement is wanted may depend on values for the heterogeneity metric. If the answer is yes, the method proceeds to stage 54 and additional sampling points are generated. A sampling density for the additional sampling points is dependent on the heterogeneity map. The additional sampling points are generated using recursive Wang tiles.

Stage 50 is repeated for the additional sampling points and the method of FIG. 3 returns to stage 52.

Once the answer to stage 52 is no (no further sampling is required), the method of FIG. 3 proceeds to stage 56.

At stage 56, for each pixel in the target image, the rendering circuitry 36 divides the value in the weighted color accumulation buffer for that pixel by the value in the accumulated weights buffer for that pixel, to obtain a final color value for the pixel. The division of value by weights may result in a normalization of color values.

Image 64 represents the weighted colors for pixels in the region that is shown in image 62. Image 66 represents the weights for pixels in the region that is shown in image 62. Image 68 represents the weighted colors when divided by the weights.

At stage 58, the rendering circuitry 36 uses the final color values for each of the image data points of the weighted color accumulation buffer to form an image. The image may be displayed to a user, for example on the display screen 26.

In some embodiments, each image data point of the weighted color accumulation buffer corresponds to a pixel of a displayed image. In other embodiments, the data in the weighted color accumulation buffer may be downsized or otherwise processed.

Using the method of FIG. 3 for rendering may reduce or eliminate aliasing in the resulting rendered image. In particular, the method of FIG. 3 avoids grid-based sampling, which is known to cause aliasing.

The method of FIG. 3 may provide a rendering method that accommodates high-definition monitors without losing performance or image quality. User experience of the image may be consistent across a range of screen resolution displays. Sampling resolution may not be tied to screen constraints.

The method of FIG. 3 makes use of a flexible sampling density. Regions having higher heterogeneity are rendered at higher resolution. Regions having higher heterogeneity may be regions having more anatomical detail. Regions having higher heterogeneity may be regions in which a more detailed rendering is desirable.

The use of a more granular sampling refinement strategy having different sampling densities at different image regions may allow for greater fine-tuning in transitional areas between high detail and low detail.

The method of FIG. 3 uses guided progressive Blue Noise to obtain sampling points. The generating of sampling points is progressive in that new sampling points may be added to previous sampling points without the previous sampling points having to be discarded. The rendering may be considered to be fully progressive.

A comparison has been performed of images rendered using the method of FIG. 3 (Blue Noise sampling with weighted splat accumulation) and images rendered from the same volumetric data set using a grid sampling method. Both methods were run on a CPU. It was found that the grid sampling image had ringing artefacts that were not present in the Blue Noise sampling image. The Blue Noise sampling method also took less time to run than the grid sampling method.

In the embodiment of FIG. 3, an image is rendered at a single desired display resolution, which is provided at stage 44. In other embodiments, the method of FIG. 3 may be used to render images from a volumetric data set at multiple resolutions. In some embodiments, an image is rendered at low resolution initially using a first number of sampling points. The image may be displayed to a user. The rendering circuitry 36 then performs a refinement process to re-render the image at a higher resolution. The rendering at higher resolution makes use of the weighted color accumulation buffer and weights accumulation buffer that were obtained during the low-resolution rendering.

The accumulation buffers remain valid in subsequent renderings of same scene.

The results for the sampling points used in the low resolution image are re-used, and additional sampling points are added. The aggregation process described above is repeated or refined for the additional sampling points to generate the high resolution image. Values stored in the accumulation buffers are updated in response to the additional sampling points being added.

Using the method of FIG. 3, if a higher-resolution image is requested, then there is no need to restart the rendering from the beginning. It is possible to continue accumulation of new samples to old buffers. The low-resolution image is thereby re-used to obtain a higher-resolution image. This contrasts with known methods in which rendering from an existing low-resolution image cannot be re-used if re-rendering the image at higher resolution.

In some circumstances, a time taken to render a high-resolution image may be greatly reduced as results of previous renders may be used in addition to new samples. It may be the case that fewer samples are needed to reach similar visual quality.

Figure 7:
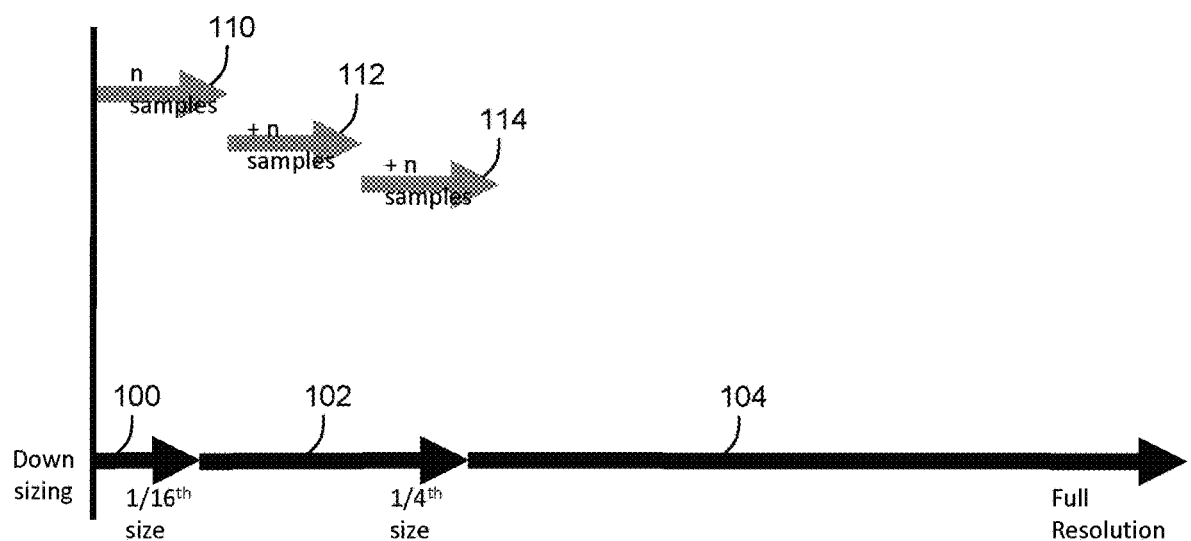
FIG. 7 is a schematic diagram illustrating progressive rendering by addition of further samples.

FIG. 7 is a schematic plot which plots a sampling process against a degree of downsizing. A horizontal axis represents resolution as a degree of downsizing, with a first arrow 100 representing an image of $\frac{1}{16}$th of full resolution; a second arrow 102 representing an image of $\frac{1}{4}$th of full resolution; and a third arrow 104 representing an image of full resolution.

Three further arrows 110, 112, 114 are used to represent different sampling stages. Arrow 110 represents a first sampling stage in which n points are sampled. The sampling of the n points results in an image of $\frac{1}{16}$th of full resolution. If it is determined (for example, at stage 52 of the process of FIG. 3) that higher resolution is required, a further n points are sampled, increasing the resolution. A still further n points may be sampled as shown by arrow 114, again increasing the resolution of the final image.

In further embodiments, a high-resolution image is rendered before a low-resolution image. The high-resolution is obtained using a first number of non-periodic sampling points. The low-resolution image is obtained by removing some of the sampling points that were used in rendering the high-resolution image, so that the set of sampling points consists of a second, reduced number of sampling points. The aggregation process is repeated or refined with the reduced set of sampling points to obtain the low-resolution image. Values stored in the accumulation buffers are updated in response to the removal of some of the sampling points. In some circumstances, a density of sampling points that is reduced from each region of the image plane may be dependent on values for the heterogeneity metric.

In the embodiment described above with reference to FIG. 3, a volume summary structure is obtained by processing the volumetric data set (for example, by segmentation) and the volume summary structure is used to obtain a heterogeneity map. In further embodiments, a heterogeneity map is obtained by using initial rendering data instead of (or in addition to) the volume summary structure. For example, in some embodiments, an initial rendering is performed using a set of initial sampling points. Data values (for example, color or intensity values) for the initial sampling points and/or the ray sampling points are used to obtain values for a heterogeneity metric. For example, values for the heterogeneity metric for a sampling point may be determined based on a variation in color or intensity values in a region around that sampling point.

In embodiments described above, a sampling density is based on values for a heterogeneity metric such that higher-heterogeneity regions are sampled at a higher sampling density. In some embodiments, a sampling density is also based on distance from a point or region of interest to the user, which may be described as the user's fixation point. The point or region of interest may be selected by the user, for example by clicking on a point or outlining a region. The point or region of the interest may be taken to be the center of the image. The point or region of the interest may be a region that the user is currently looking at. The region that the user is looking at may be obtained from eye-tracking information. Eye-tracking information may be available in, for example, virtual reality systems.

A variation in sampling density with distance from the point or region of interest may be applied by biasing values for the heterogeneity metric by a value that is proportional to an estimated distance from the point or region of interest. By biasing the heterogeneity metric, sampling densities may in general be higher for regions of the image that are nearer the point or region of interest, while still taking account of heterogeneity in the image. In some embodiments, a significance required to prompt further refinement of an image region is biased by a value proportional to the estimated distance from the user's fixation point. A heterogeneity threshold used to determine whether further rendering is required may be higher for regions that are further from the fixation point.

In some embodiments, the splat weighting for a sampling point is a function of the heterogeneity at that sampling point and the heterogeneity of a pixel of interest, in addition to the splat weighting being dependent on the distance from the sampling point to the pixel. For example, we consider two regions of the image plane (or of the heterogeneity map) that border each other. A first region has high heterogeneity and so has been sampled using many sampling points. A second region has lower heterogeneity and so has been sampled using fewer sampling points. It may be considered desirable that contributions from the sampling points in the high heterogeneity regions do not bleed into the low heterogeneity region (and vice versa) due to the splatting process. In some embodiments, this effect is avoided by incorporating heterogeneity into how the weighting functions are computed, such that regions of similar heterogeneity yield higher weights, while areas of greatly differing heterogeneity yield lower weights.

In some embodiments, splat pixel weighting is biased by a distance from a focal plane. Pixels that are distant from the focal plane may be made blurred and out of focus, for example by applying a shallower weighting function that spreads out color from a sampling point over a greater number of pixels. Detail on the focal plane may remain sharp.

In rendering an image, a notional focal distance may be determined, which may be considered to correspond to a distance from a lens as used in photography. The notional focal distance may be obtained by tracking the distance travelled by a ray. When performing a volume render, a depth to which the ray penetrated into the volume may be stored in a z buffer. The z buffer records the third, z, dimension in image space. The depths stored in the z buffer may be used in conjunction with the notional distance to the lens to alter the weighting distance. A virtual focal plane may be defined as a plane parallel to the image plane, at a distance equal to the notional focal distance.

Areas where the z depth is similar to the notional focal distance may have a steeper weighting fall-off than areas which are far from a focal plane, and may therefore appear sharper and less blurred.

In embodiments described above, a single image processing apparatus receives the volumetric data set and renders an image from the volumetric image data set. In other embodiments, a rendering process may be split across two or more computing apparatuses, for example two or more computers in a network.

In one embodiment, a first part of a rendering process is performed by a server and a second part of the rendering process is performed by a client computing device. The client computing device is remote from the server and is connected to the server via a wired or wireless network. The client device may be, for example, a mobile device such as a mobile phone, tablet or laptop.

In the first part of the rendering process, the server receives a volumetric data set and processes it to obtain a volume summary structure. The server may also receive a selection of a display resolution. The server receives or generates a set of initial sampling points that are generated using recursive Wang tiles. The server samples the volumetric data set using rays corresponding to each of the initial sampling points to obtain a set of color values. The server also samples the volume summary structure to obtain a heterogeneity map.

The server sends the color values for the initial sampling points over the network to the client device. In the second part of the rendering process, the client device carries out the splatting of the color values for the initial sampling points onto a weighted color accumulation buffer and also accumulates weights in a weights accumulation buffer.

Because the initial sampling points have been obtained using recursive Wang tiles, the server may not need to send the positions of the initial sampling points to the client device. The client device may be able to obtain or store a set of initial sampling point positions locally by using recursive Wang tiles.

If further sampling points are needed, the client device sends a request to the server, which determines the positions of the further sampling points using recursive Wang tiles. The server uses the heterogeneity map to determine a density of the further sampling points for different regions of the image. The server then renders the further sampling points and sends color values for the further sampling points to the client device. The client device updates the weighted color accumulation buffer by splatting the color values for the further sampling points onto the weighted color accumulation buffer. The client device updates the weights accumulation buffer by accumulating the weight values for the further sampling points in the weights accumulation buffer.

If a resolution required by the client device increases, the client device sends a request for more sampling points to the server, which performs a further rendering.

In other embodiments, there may be a different division between which steps are performed by the server and which are performed by the client device.

In some embodiments, rendering over a network may be speeded up by sending sparse pixel lists rather than a full canvas. The client device may perform splatting operation locally. WebGL may be well suited to the task of splatting locally.

Sampling point position may not be transmitted. Blue Noise Wang tiles may be used to reconstruct positions on the client device.

Rendering over the network may potentially result in a very significant reduction in network usage. The server may asynchronously queue pixels for the client device to accumulate into its visualizations when time allows.

Splitting rendering between a remote device (for example a server) and a local client device (for example, a mobile device) may facilitate communication of high-resolution image when network bandwidth is limited. It may not be necessary to send an entire volumetric data set over the network. Values for a limited set of sampling points may be set over the network. A saving in bandwidth may be particularly noticeable when the final image required is relatively low resolution (for example, for display on a mobile phone).

In some circumstances, methods described above may greatly reduce aliasing artefacts in VR views.

A user may be provided with an improved interactive experience. When a user is manipulating image data in an interactive mode (for example, by changing a viewing angle or a pre-set) it may be the case that a lower-resolution image is first presented to the user, followed by a higher-resolution image. Methods described above may provide a smooth refinement from interactive to full-detail. Additional sampling points may be added to an existing render rather than the whole render being re-done.

Methods described above may be used to produce diagnostic-quality slab renders or intensity projection renders for 4 k (or 8 k) monitors on multi-user systems. Interactive rendering may be enabled on mobile devices. Rendering for iPads or other tablet devices may be provided.

In some embodiments, the rendering process may make use of machine learning. For example, in one embodiment a neural network is trained to generate a volume summary map from volumetric data set. The neural network is provided with a large number of training volumetric data sets, and may also be provided with volume summary maps for some or all of the training volumetric data sets. From the training volumetric data sets, the neural network is trained to produce volume summary maps. Stage 42, computing the volume summary structure, may be performed using a trained neural network.

In other embodiments, a neural network (which may be the same neural network as that used to produce volume summary maps) is trained to use machine learning to perform weighted accumulation. In some embodiments, machine learning is used to produce a better weighting function. In other embodiments, machine learning replaces weighted accumulation as the resampling method.

In a further embodiment, a neural network (which may be the same neural network as that used to produce volume summary maps and/or perform weighted accumulation) is trained to determine positions of sampling points based on the heterogeneity map.

In another embodiment, a neural network is trained using sets of training data, each comprising a heterogeneity map and data values for a plurality of sampling points, ray sampling points and/or image data points. The training data may also comprise the positions for the blue noise based sampling points. The neural network may be trained to output values for sampling points, ray sampling points and/or image data points in dependence on a heterogeneity map.

Certain embodiments provide an image processing apparatus comprising processing circuitry configured to: acquire volume data for rendering and a heterogeneity map based on the volume data, generate first data based on random-sampling points and the heterogeneity map, generate second data by splatting an image voxel value of sampling points included in the first data, generate third data based on the sampling points and a distance from the image voxel to the sampling points, render the volume data by correcting the second data based on the third data.

The sampling points may be based on blue-noise patterning.

Certain embodiments provide a method for visualization of volume data using a set of samples distributed in a pattern consistent with Blue Noise, where a heterogeneity measure is computed using min-max information, transfer function gradients and 3D wavelet indices, and which is then used to decide the local sampling density of a second set of samples distributed in a pattern consistent with Blue Noise. The samples are then resampled into an image through use of weighted splat accumulation.

The sampled Blue Noise pattern may be computed through use of progressive blue noise Wang Tiles.

A heterogeneity value of each sample point may be biased by a value proportional to the distance of that point from a focal plane to produce a Depth-of-field approximation.

A set of samples produced by a previous invocation of the method may be retained and reused in a second invocation.

The heterogeneity measure may be biased by a value proportional to the estimated distance from the user's fixation point.

A splat weighting for a pixel may be a function of the sampled point heterogeneity and the heterogeneity for the pixel of interest in addition to the distance from the sample point.

Certain embodiments provide a method for visualization of volume data using a set of samples distributed in a pattern consistent with Blue Noise, where the sampled values are accumulated into buffers through use of a weighted splat accumulation operation, and where the resulting change in values for each image region are tracked, and the regions where significant changes are found are marked to receive further samples, distributed in a pattern consistent with Blue Noise.

The sampled Blue Noise pattern may be computed through use of progressive blue noise Wang Tiles.

A significance required to prompt further refinement of an image region may be biased by a value proportional to the distance of that point from a focal plane.

A set of samples produced by a previous invocation of the method may be retained and reused in a second invocation.

A significance required to prompt further refinement of an image region may be biased by a value proportional to the estimated distance from the user's fixation point.

Methods are described above with reference to images. Operations described above as being performed on images may in practice be performed on sets of image data that are representative of those images. For example, operations may be performed on data comprising sets of pixel or voxel positions and associated intensities. In many cases, operations are performed on image data without the corresponding images being displayed.

Although particular orderings of method steps are described above, in further embodiments method steps may be performed in any suitable order. One or more of the steps described above may be omitted, or further steps may be added. Any suitable rendering methods and data processing methods may be used.

Methods described above with regard to color values may be instead performed using any suitable image values, for example intensity values or texture values. Any suitable rendering process may be used to obtain two-dimensional or three-dimensional images.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An image processing apparatus for generating an image from volumetric data comprising:
   a medical imaging scanner to generate a volumetric data set; and
   processing circuitry configured to:
      obtain the volumetric data set from the scanner;
      perform ray-casting processing on the volumetric data set to obtain a heterogeneity map;
      determine positions of a set of non-periodic sampling points using the heterogeneity map;
      generate from the volumetric data set a set of sampled data values based on the determined positions of the non-periodic sampling points; and
      generate an image data set by performing an aggregation process to generate a set of image data points from the set of sampled data values, wherein
   the heterogeneity map comprises a representation of a value of a heterogeneity metric as a function of position, and
   the ray-casting process comprises:
      casting a plurality of rays into the volumetric data set, and
      for each of a plurality of ray sampling points along each of the rays, identifying a respective region in which the ray sampling point is located and determining a respective value of a ray-region heterogeneity metric for the region in which the ray sampling point is located, and
      for each ray, using values of the ray-region heterogeneity metric for the ray sampling points to determine the value of the heterogeneity metric for the ray.

2. An image processing apparatus according to claim 1, wherein the aggregation process comprises a weighted aggregation process.

3. An image processing apparatus according to claim 1, wherein the aggregation process comprises a weighted splat process.

4. An image processing apparatus according to claim 1, wherein the process of generating from the volumetric data set the set of sampled data values comprises performing a ray-casting or image rendering process for the determined positions.

5. An image processing apparatus according to claim 1, wherein the respective heterogeneity metric for each region is determined based on variation in value of at least one of color, intensity, transfer function, wavelet index, and segmentation within each region.

6. An image processing apparatus according to claim 1, wherein at least one of:
   a) the positions of the set of non-periodic sampling points are determined using a blue noise sampling process; and
   b) the positions of the set of non-periodic sampling points are in accordance with a blue noise distribution.

7. An image processing apparatus according to claim 6, wherein the blue noise sampling process uses Wang tiles to determine the non-periodic sampling points.

8. An image processing apparatus according to claim 1, wherein a distribution of the sampling points is dependent on the heterogeneity map such that an average concentration of sampling points varies with position in dependence on the value of a heterogeneity metric in the heterogeneity map.

9. An image processing apparatus according to claim 1, wherein the set of non-periodic sampling points consists of a first number of non-periodic sampling points, and the processing circuitry is configured to perform a refinement process that comprises:
   adding further sampling points to the set of non-periodic sampling points;
   generating further sampled data values based on the further sampling points; and
   using said further sampling points, repeating or refining the aggregation process to generate the set of image data points.

10. An image processing apparatus according to claim 9, wherein the aggregation process to generate the set of image data points comprises a weighted splat process, and the repeating or refining comprises repeating or refining the weighted splat process for the further sampling points.

11. An image processing apparatus according to claim 1, wherein the set of non-periodic sampling points consists of a first number of non-periodic sampling points; and
   the processing circuitry is configured to perform a refinement process that comprises:
   removing sampling points from the set of non-periodic sampling points so that the set of sampling points consists of a second, reduced number of sampling points; and
   using said second, reduced number of sampling points, repeating or refining the aggregation process to generate the set of image data points.

12. An image processing apparatus according to claim 1, wherein the processing circuitry is configured to perform said process of generating an image data set in dependence on a selected resolution thereby to generate an image data set with said selected resolution.

13. An image processing apparatus according to claim 1, wherein the aggregation process to generate the set of image data points comprises a weighted splat process, and the processing circuitry is configured to maintain in an at least one buffer values of at least one of intensity, color and weight, and to update said values in response to sampling points being added or removed.

14. An image processing apparatus according to claim 1, further comprising a data store that stores the determined positions of the set of non-periodic sampling points and/or the set of sampled data values,
   wherein the processing circuitry is configured to perform a refinement process to refine the image data set, the refinement process including adding or removing data points to the set of non-periodic sampling points and/or the set of sampled data values stored in the data store.

15. An image processing apparatus according to claim 14, wherein the data store comprises a buffer.

16. An image processing apparatus according to claim 1, wherein the processing circuitry is configured to receive via a network from a server or other remote source, at least one of: the heterogeneity map, the positions of the set of non-periodic sampling points, and the generated sampled data values; and wherein the processing circuitry is configured to perform at least the generating of the image data set using the aggregation process at a local computer remote from the server or other remote source.

17. An image processing apparatus according to claim 1, wherein the volumetric data comprises computerized tomography (CT) data, magnetic resonance (MR) data, X-ray data or other medical imaging data.

18. An image processing apparatus according to claim 1, wherein the processing circuitry is configured to use a trained network or other machine learning process to at least one of: obtain the heterogeneity map based on the volumetric data set, perform the determining of positions of the non-periodic sampling points from the heterogeneity map.

19. An image processing apparatus according to claim 1, wherein the processing circuitry is configured to:
   obtain a volume summary structure providing summary information about the volume data set; and
   determine the respective value of the ray-region heterogeneity metric for each region using the volume summary structure.

20. A method of generating an image from volumetric data comprising:
   obtaining a volumetric data set;
   perform ray-casting processing on the volumetric data set to obtaining a heterogeneity map;
   determining positions of a set of non-periodic sampling points using the heterogeneity map, wherein the heterogeneity map comprises a representation of a value of a heterogeneity metric as a function of position;
   generating from the volumetric data set a set of sampled data values based on the determined positions of the non-periodic sampling points; and
   generating an image data set by performing an aggregation process to generate a set of image data points from the set of sampled data values,
   wherein the ray-casting process comprises:
      casting a plurality of rays into the volumetric data set, and
      for each of a plurality of ray sampling points along each of the rays, identifying a respective region in which the ray sampling point is located and determining a respective value of a ray-region heterogeneity metric for the region in which the ray sampling point is located, and
   for each ray, using values of the ray-region heterogeneity metric for the ray sampling points to determine the value of the heterogeneity metric for the ray.

* * * * *